United States Patent [19]

Warren et al.

[11] Patent Number: 4,914,591

[45] Date of Patent: Apr. 3, 1990

[54] METHOD OF DETERMINING ROCK COMPRESSIVE STRENGTH

[75] Inventors: Tommy M. Warren, Coweta; Warren J. Winters, Tulsa; Ernest C. Onyia, Broken Arrow, all of Okla.

[73] Assignee: Amoco Corporation, Chicago, Ill.

[21] Appl. No.: 173,514

[22] Filed: Mar. 25, 1988

[51] Int. Cl.$^4$ .......................... G01N 33/24; E21B 7/04
[52] U.S. Cl. ....................................... 364/422; 73/818; 73/152; 73/783; 367/25; 175/40; 175/50
[58] Field of Search .................. 364/420; 73/818, 152, 73/783; 175/40, 50; 367/25

[56] References Cited

U.S. PATENT DOCUMENTS

| | | | |
|---|---|---|---|
| 4,396,071 | 8/1983 | Stephens | 175/50 |
| 4,599,904 | 7/1986 | Fontenot | 73/783 |
| 4,627,276 | 12/1986 | Burgess | 73/151 |
| 4,733,733 | 3/1988 | Bradley | 175/45 |

OTHER PUBLICATIONS

Warren, T. M., "Penetration-Rate Performance of Roller-Cone Bits", SPE Drilling Engineering, Mar. 1987, pp. 9-18.
Winters et al., "Roller Bit Model with Rock Ductility and Cone Offset", 62nd Annual Technical Conference and Technical Conference and Exhibition of Petroleum Engineers, Dallas, Tx., Sep. 27-30, 1987.

Primary Examiner—Jerry Smith
Assistant Examiner—Gail O. Hayes
Attorney, Agent, or Firm—Scott H. Brown; Fred E. Hook

[57] ABSTRACT

A method is disclosed for determining rock compressive strength of a subterranean formation penetrated by a wellbore. A mathematical model of a drill bit and an estimate of rock ductility of a particular subterranean formation in conjunction with weight-on-bit (WOB), bit rotational speed RPM, and rate of penetration (ROP) are used as inputs. From the above inputs, the rock compressive strength can be determined while the wellbore is being drilled or afterwards. A depth correlated log can be generated of rock compressive strength that can be compared to other logs obtained from adjacent wellbores to obtain a refined estimate of the depth of a particular subterranean formation feature. Further, the above method can be utilized for obtaining an indication of bit wear or bit damage while the bit is drilling a wellbore by comparing a first rock compressive strength log of a wellbore to a rock compressive strength log being generated while the drill bit is actually drilling a second wellbore. Any significant deviation between the two logs provides an indication of bit wear or bit damage.

7 Claims, 5 Drawing Sheets

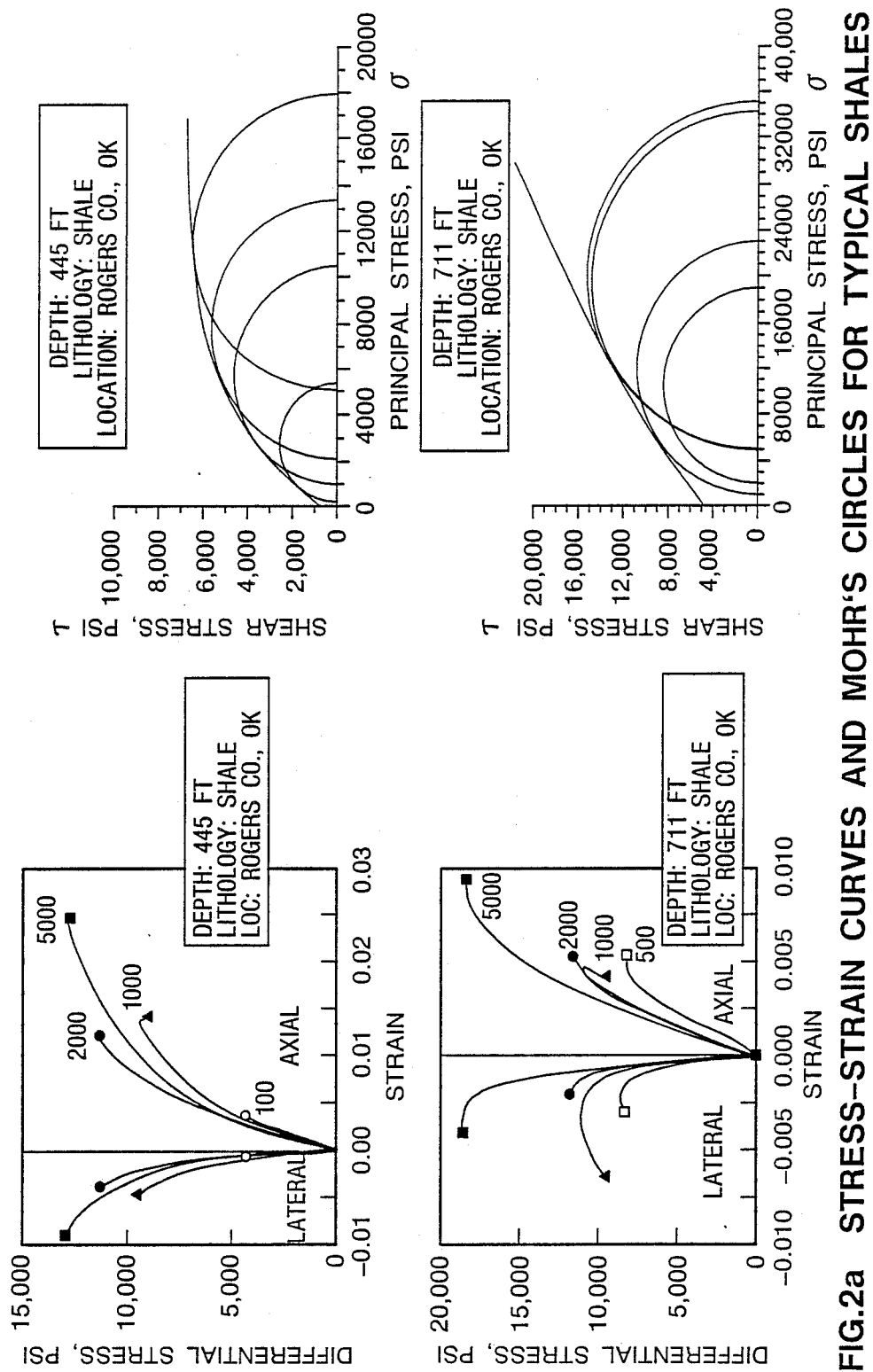
FIG.2a STRESS-STRAIN CURVES AND MOHR'S CIRCLES FOR TYPICAL SHALES

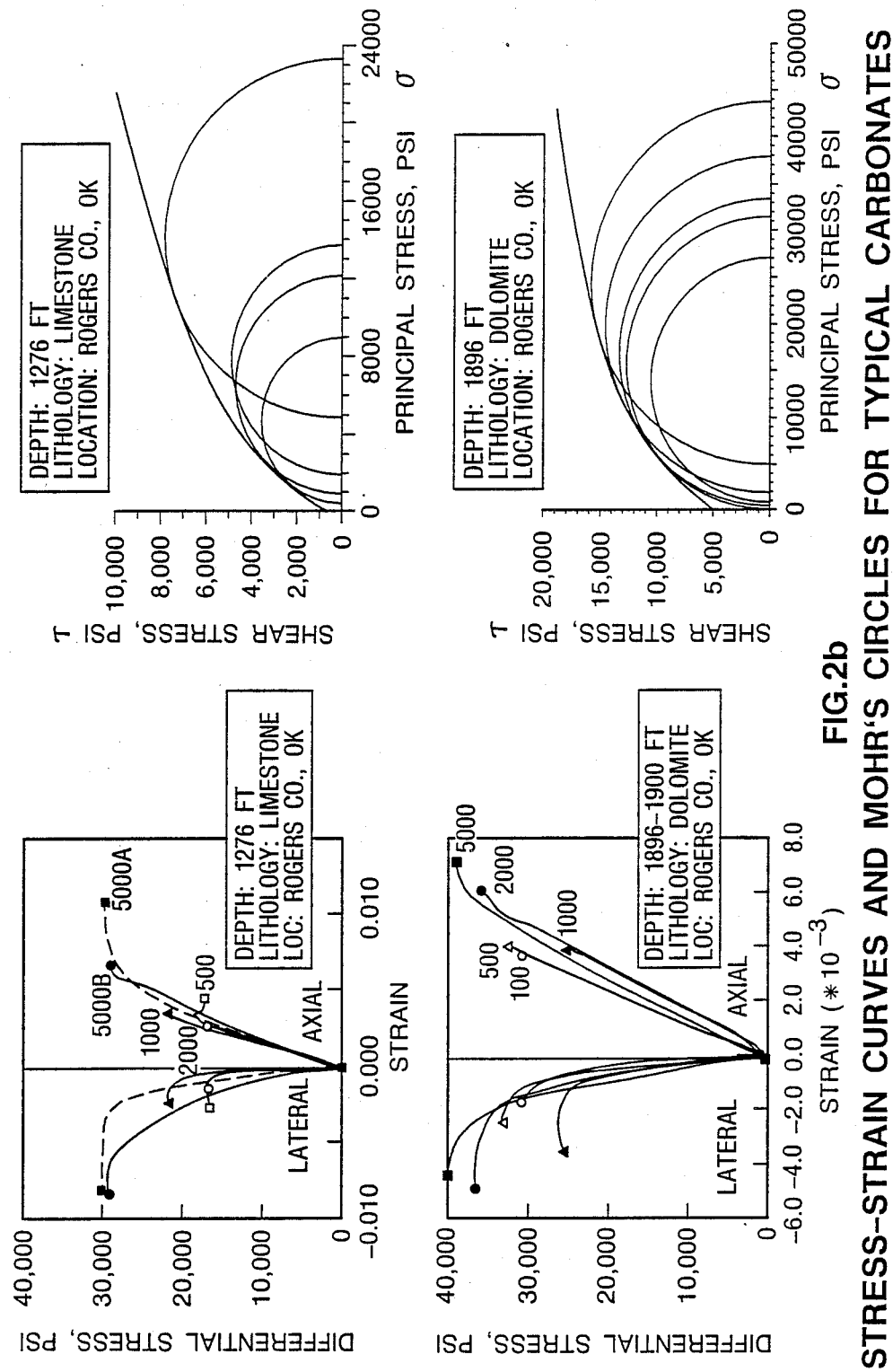
FIG.2b    STRESS-STRAIN CURVES AND MOHR'S CIRCLES FOR TYPICAL CARBONATES FIELD DATA IS EVALUATED WITH THE ROLLER BIT MODEL TO PRODUCE A CONTINUOUS ROCK STRENGTH LOG WHICH CORRELATES CLOSELY TO INDEPENDENTLY MEASURED TRIAXIAL COMPRESSIVE STRENGTHS SIMILAR ROCK STRENGTH LOGS ARE COMPUTED FROM FIELD DATA OBTAINED WITH ENTIRELY DIFFERENT STYLES OF BITS

METHOD OF DETERMINING ROCK COMPRESSIVE STRENGTH

BACKGROUND OF THE INVENTION

1. Field of the Invention

The present invention relates to a method of determining rock compressive strength and, more particularly, to such a method that utilizes a mathematical model of the drill bit and rock ductility.

2. Setting of the Invention

The knowledge of a subterranean formation's compressive strength is important in the proper selection and operation of drilling equipment. For example, the compressive strength of a formation material determines what type of drill bit to utilize and what weight on bit (WOB) and rotational speeds (RPM) to utilize. As is well known, an estimate of the compressive strength of a subterranean formation material can be obtained from geological and geophysical information, such as well logs from adjacent wellbores. Various mathematical modeling techniques have been developed to determine an estimate of compressive strength from these well logs, but there have been no methods of determining what the formation material's compressive strength is while drilling.

A log of rock compressive strength correlated to a depth within a wellbore could be very beneficial. Such a log could be generated after or while drilling, which could then be utilized to depth correlate other logs from adjacent wellbores, as well as provide an indication of bit wear or bit damage while a drill bit is drilling the wellbore. There is no known method for accomplishing the generation of such a log. U.S. Pat. No. 4,627,276 describes a method of measuring bit wear while drilling but does not disclose or suggest generating a log of rock compressive strength and utilizing such a log to determine bit wear or bit damage.

SUMMARY OF THE INVENTION

The present invention has been contemplated to meet the above described needs by providing a method of determining the rock compressive strength of one or more subterranean formations penetrated by a wellbore. In this method, certain operating characteristics of a drill bit (to be utilized to drill a wellbore) are obtained, as well as an estimate of the rock ductility of the one or more subterranean formations. While the drill bit is drilling the wellbore through the subterranean formation(s), the weight on bit (WOB), the drill bit's rotational speed (RPM), and the drilling rate of penetration (ROP) are recorded. From this information, the rock compressive strength of the subterranean formation(s) can be determined in accordance with equations set forth below.

After the rock compressive strength for a particular subterranean formation has been determined, it can be correlated with depth of the wellbore to provide a log of compressive strength. This log can then be compared to other logging information from adjacent wellbores to obtain a refined estimate of the depth of certain subterranean features. Further, as the log of rock compressive strength is obtained, it can be compared to one or more preexisting logs of rock compressive strength from adjacent wellbore to provide an indication of the drill bit's performance while drilling, such as bit wear or bit damage.

BRIEF DESCRIPTION OF THE DRAWINGS

FIG. 2A is a graph of stress-strain curves and Mohr's circles for typical shales.

FIG. 2B is a graph of stress-strain curves and Mohr's circles for typical carbonates.

DETAILED DESCRIPTION OF THE PREFERRED EMBODIMENTS

Figure 1A:
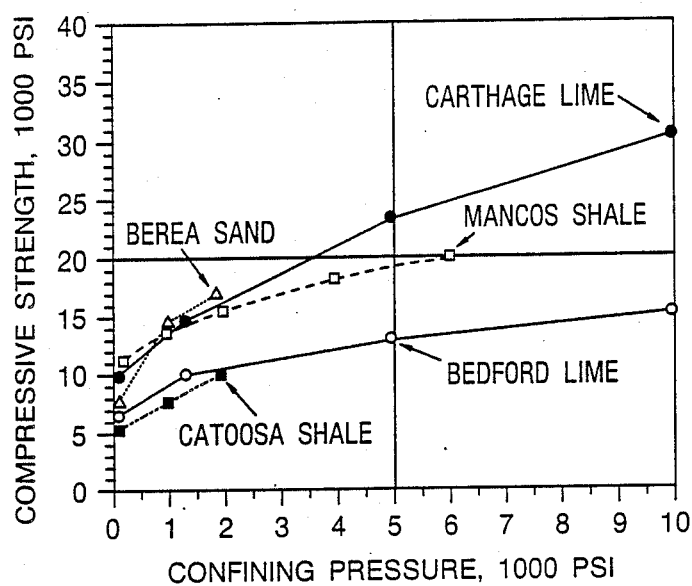
FIG. 1A is a graph of rock compressive strength vs confining pressure for different rock types.

The present invention provides a method of determining rock compressive strength of one or more subterranean formations penetrated by a wellbore. As will be described herein below, certain operating characteristics of a drill bit (to be utilized to produce the wellbore) are obtained for utilization in this method, as well as an estimate of rock ductility of the one or more subterranean formations. During the drilling of the wellbore, the weight-on-bit (WOB) and the drill bit's rotational speed (RPM) are recorded. This information, as well as the recorded values of the wellbore's mud flow rate (Q), mud density (P), mud viscosity ($\mu$), and the drill bit's penetration rate (R) are utilized in determining the rock compressive strength of the one or more subterranean formations in accordance with this invention. As will become apparent to those skilled in the art, the method of the present invention can be carried out during drilling to provide a real-time or approximately real-time determination of rock compressive strength, or after any or all phases of the drilling is (are) completed to provide a historical database for use in well completion operations on the wellbore or subsequent adjacent or remote wellbores. Further, the calculation of any or all of the portions of the method requiring mathematical determinations can be accomplished by one or more persons alone or in combination with or all by a programmable digital computer, as is well known to those skilled in the art.

The method of determining rock compressive strength starts with a determination of at least four bit design constants called "operating characteristics" of a drill bit to be utilized in drilling the wellbore through the subterranean formation(s). These four design constants are: "a" related to bit tooth indentation, "b" related to bit tooth configuration, "c" related to fluid hydraulics across the bit, and "$\phi$" related to bit cone offset. These design constants are well known in the art and are easily obtained by those skilled in the art. For example, see Winters, W. J., et al., "Roller Bit Model with Rock Ductility and Cone Offset," SPE 16696, presented at the Annual Technical Conference of the Society of Petroleum Engineers, Dallas, Tex. (Sept. 27–30, 1987).

For example, a roller cone drill bit can be tested in a laboratory in the following manner to yield the required bit design constants for use in determining the rock compressive strength in accordance with the present invention. A drill bit is tested by measuring its rate of penetration as the applied weight-on-bit (WOB) is increased in a stepwise fashion. The rotary speed (RPM), flowrate, and borehole pressure are held constant during each WOB response test. This procedure is repeated for at least two rock types of known compressive strength and ductility and for at least two rotary speeds and flowrates for each rock type. Preferably, these tests are conducted at an elevated borehole pressure, such as about 1200 psi.

Utilizing nonlinear regression analysis on the above obtained laboratory data for the drill bit yields the design constants from the equation $$\frac{1}{R} = \frac{a\sigma^2 D^3 \epsilon}{NW^2} + \frac{\phi\sigma D^2}{NW\epsilon} + \frac{b}{ND} + \frac{c\rho\mu D}{I_m} \quad (1)$$

where values for all of the parameters other than the bit design constants are measured in the laboratory tests. It has been found that the design constants remain generally invariant over the normal range of values for other parameters that are specified. The laboratory data for a drill bit can be reduced to a table of four coefficients for each IADC bit category. As an example, Table 1 is provided.

TABLE 1

| IADC CODE | BIT DESIGN CONSTANTS | | | |
|---|---|---|---|---|
| | BIT CONSTANTS+ | | | |
| | a | Φ | b | c |
| 2-1-1 | .0083 | .0248 | 8.763 | .0023 |
| 4-2-7 | .0101 | .0123 | 1.303 | .0020 |

+referenced to 1200 psi borehole pressure.

Figure 1B:
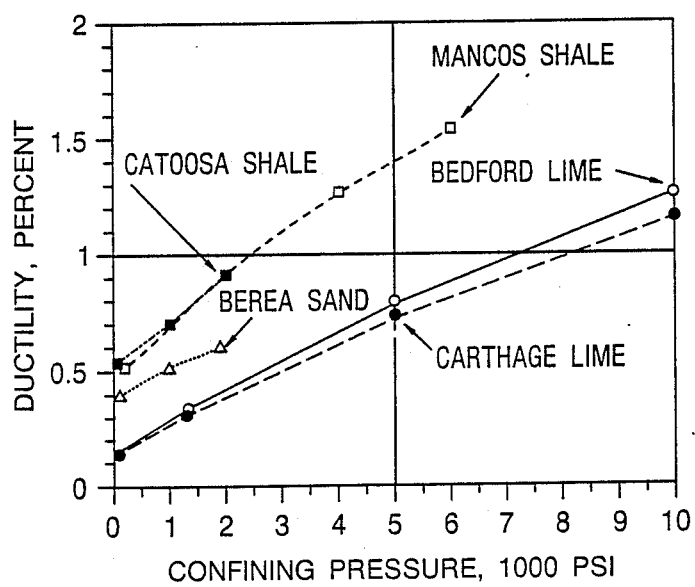
FIG. 1B is a graph of rock ductility vs. confining pressure for the rock types of FIG. 1A.

Another parameter needed for use in the method of the present invention is an estimate of rock ductility. In the absence of direct measurements of rock ductility taken from core samples from the wellbore being drilled or adjacent wellbores, the needed rock ductility values can be estimated. Reasonable estimates can be made based upon published literature values for various lithologies expected to be encountered in drilling the wellbore. Examples of the rock ductility of typical oil field rocks are shown in FIGS. 1B and 2B.

Additional parameters needed for use in the method of the present invention are the recorded and depth correlated values of weight-on-bit (WOB), the drill bit's rotational speed (RPM), the penetration rate (R), and the drilling fluid's flow rate (Q), density ($\rho$), and viscosity ($\mu$). The parameters are easily obtained in analog or digital form while drilling, as is well known in the art from sensors on the drill rig and thus can be recorded or transmitted real-time or delayed to a microprocessor utilized in the method of the present invention. The drilling fluid's density and flowrate are utilized to compute the values for modified fit impact force ($I_m$), as is well known in the art. For example, see Warren, T. M., "Penetration Rate Performance of Roller Cone Bits, *SPE Drilling Engineering* (March 1987), 9–18.

Utilizing all of the above parameters, the rock compressive strength can be determined through the use of the following equation:

$$\sigma = \quad (2)$$

-continued $$\left[ \frac{W^2}{aD^2\epsilon} \left[ \frac{\frac{N}{R} - \frac{b}{D} - \frac{cN\rho\mu D}{I_m}}{D} + \frac{\phi^2}{4a\epsilon} \right] \right]^{.5} - \frac{\phi W}{2aD\epsilon^2}$$

wherein:

| Factor | Definition | Units of Dimensions |
|---|---|---|
| Φ | cone offset coefficient | 1/L |
| ρ | mud density | lb/gal |
| σ | rock compressive strength | psi |
| μ | mud viscosity | cp |
| a,b,c | bit design constants | dimensionless |
| D | bit diameter | inches |
| $I_m$ | modified jet impact force | lb$f$ |
| N | rotary speed | rev/min |
| R | penetration rate | ft/hr |
| W | weight-on-bit | klb |
| ε | rock ductility | dimensionless, % |

A log of rock compressive strength can be generated by having sensors on the drilling rig measure the weight-on-bit (WOB), RPM and rate of penetration (ROP) and input these into a programmable digital microprocessor or computer at the rig site or transmit some to a remote computing facility. The estimated rock ductility and the four design constants for the particular bit can then be inputted. The microprocessor can be activated on a continuous, real-time basis or at a later time to calculate the rock compressive strength from these input parameters and generate a depth correlated log that can be visually displayed or provided in a hardcopy form to the drilling operator. Obviously, the log can be recorded in analog or digital form and be processed or even reprocessed later at another location.

A rock compressive strength log generated utilizing the method described above is shown in FIG. 3. Data was recorded over a 3000 ft interval in Rogers County, Oklahoma from a wellbore designated as DM No. 2 Three 8.5 in. bits with respective IADC codes 4-3-7, 5-3-7, and 6-2-7 were used to drill the logged interval. The above bits were first tested in a laboratory to determine their respective four design constants. Once per foot averages of WOB, rotary speed, ROP, and drilling fluid density, viscosity, and flow rate were continuously recorded during the field test. As shown, the computed bottomhole rock strengths range from 3000–30,000 psi in the Pennsylvanian to Pre-Cambrian geological zones.

Figure 3:
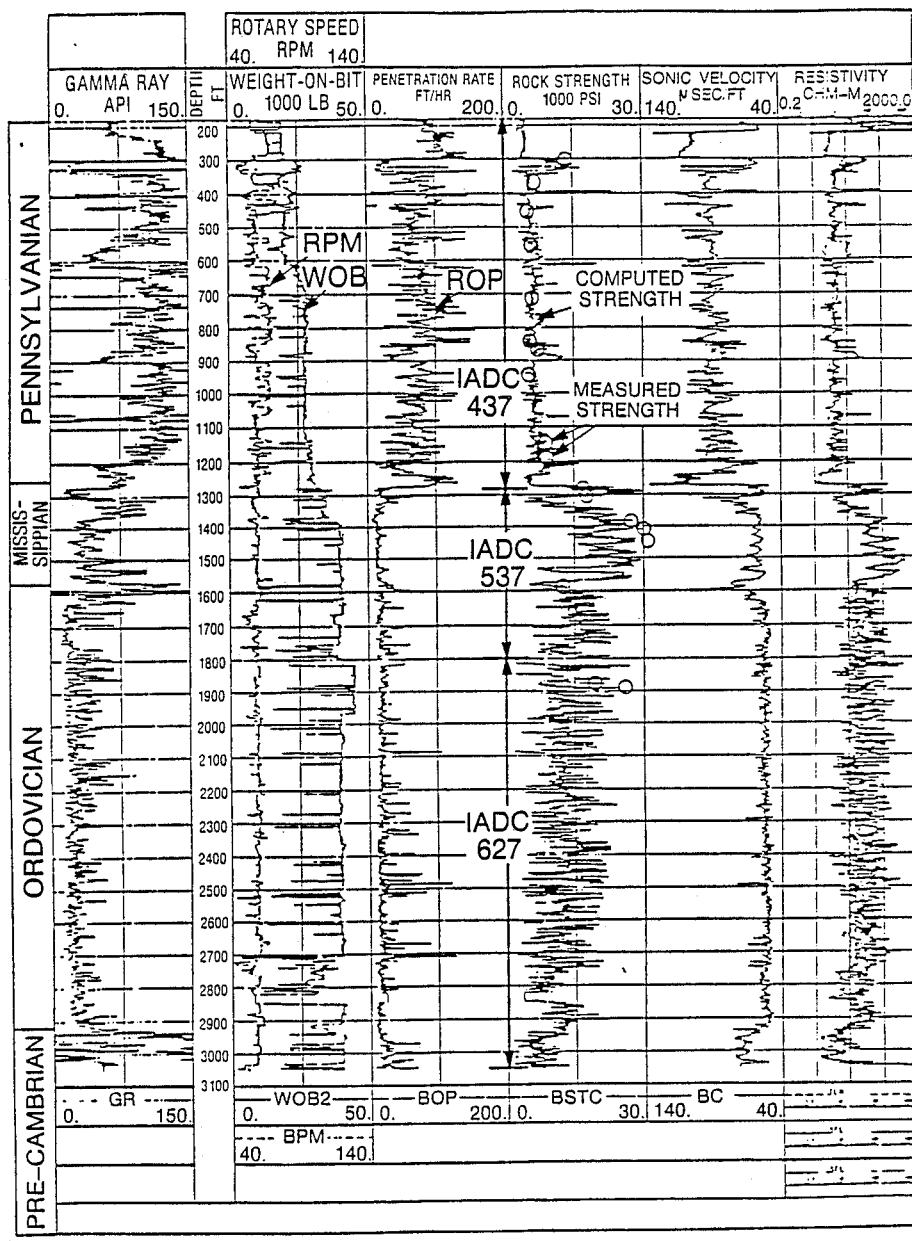
FIG. 3 is a depth correlated log of computed rock strength compared to independently measured rock strength.

The computed rock strengths from DM No. 2 appear to be reasonable with respect to formation lithology and related log properties, but an independent measure of rock strength was conducted to quantify the method's accuracy. Therefore, 18 vertically oriented core samples were obtained from an adjacent test hole that was drilled to a depth of 1900 ft, approximately 100 yards from the DM No. 2 location. All 18 rock samples were tested in a triaxial load cell to determine their mechanical properties at confining pressures ranging from about 100 psi to about 5000 psi, as is well known in the art. The computed strengths and measured strengths from DM No. 2 and the 18 cores are shown in FIG. 3, where it can be seen that a close match is obtained between the measured triaxial rock strengths and computed drilling strengths of the present invention.

Figure 4:
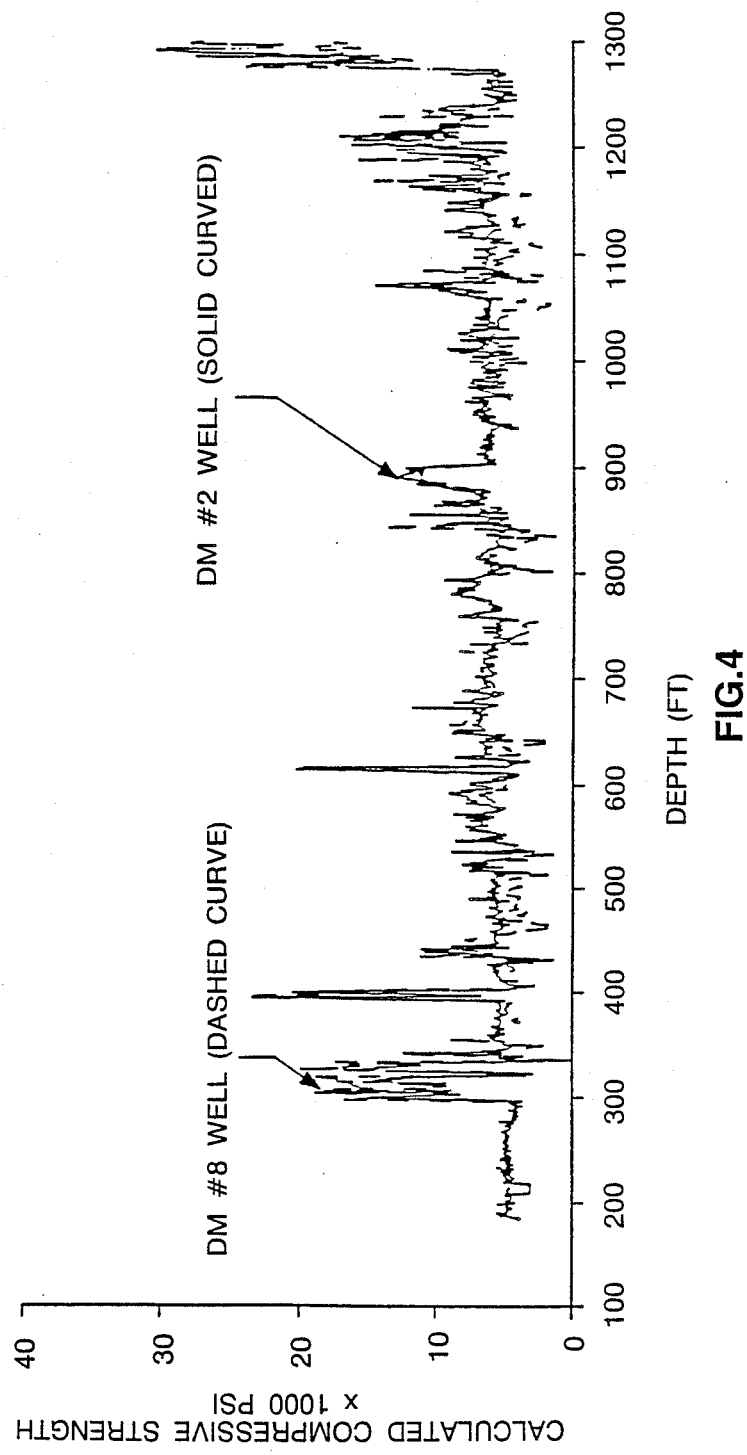
FIG. 4 is a depth correlated log of rock compressive strength from two wells.

An additional effort was made to qualify the method by drilling another test hole about 10 yards from the DM No. 2 location. This hole, designated as DM No. 8, was drilled to a 1300 ft depth with a different drill bit size and different design and was operated at higher rotary speeds, lower WOB levels, and higher drilling fluid flow rates. A rock compressive strength log was computed utilizing the methods of the present invention from the DM No. 8 data. FIG. 4 shows that a close match was obtained between the rock strength logs of DM No. 2 and DM No. 8. This result, in conjunction with the above demonstrated correlation to triaxial rock strengths, demonstrates that the method of the present invention can be used to accurately determine rock compressive strengths with field test data and predict the bit performance from offset well data.

Further uses of the method include utilizing the data recorded from two or more offsetting wells to determine not only the compressive strength but also the ductility of the rock. Whereas in Eq. (2), it is necessary to estimate or assume values for ductility in order to solve the equation for values of rock compressive strength, when data are obtained from two or more offsetting wells than a simultaneous solution of two or more equations (Eq. (2)) containing two unknowns (compressive strength and ductility) can be effected to arrive at a mathematically determined set of compressive strength and ductility values for each subterranean interval.

Other uses of a log generated in accordance with the method can include correlating the log with other well logs, such as logs of sonic velocity, resistivity, density, etc., to provide a better estimate of subterranean features, i.e., provide a depth correlation between a well being drilled and a previously drilled well. Identifying where a particular formation feature is appearing within the wellbore being drilled is extremely important and useful, for example, as for determining where the drill bit actually is within the wellbore and predicting when a particular type drill bit should be changed to another type of drill bit that would drill better in a particular formation. Also, this correlation is useful in picking casing points, logging points, fault zones, etc. This method of correlation can be accomplished by an individual or by utilizing a programmable digital computer wherein the rock compressive strength log obtained from a first well is continuously, on a real-time basis, or afterwards compared to a log generated from a second well. The depths where certain subterranean features appear can be compared to provide a depth correlation indicative of whether or not the formations/features encountered in the well being drilled are above, at, or below the expected locations and by how much.

In the case where a rock compressive strength log is generated for a first well, this log can be used as a monitor of bit condition while drilling a second well. In other words, deviation between previously obtained log values and log values obtained for the same formation with the same type of bit can provide an indication of reduced bit drilling efficiency, such as that due to bit wear. Also, sudden deviations can provide an indication of catastrophic damage to the bit. Similarly, deviations between other log parameters, such as gamma ray, sonic velocity, and resistivity and the calculated compressive strength can identify bit performance degradation. This method can be accomplished by having a log of rock compressive strength generated for one or more adjacent wellbores. The log of the rock compressive strength of the well being drilled is then continuously generated and the two logs can be compared between themselves or in addition to other logs, either by hand or using comparative functions employable by a programmable digital computer. Deviations between the two logs of more than, for example, five percent, can indicate that the cones or the cutters on the drill bit are wearing and by how much. If the bit wear becomes excessive or bit damage is detected, an alarm can be activated and the bit can be removed and replaced.

Wherein the present invention has been described in particular relation to the drawings attached hereto, it should be understood that other and further modifications, apart from those shown or suggested herein, may be made within the scope and spirit of the present invention. It should be understood that whereas as the triaxial compression test has been selected as the technique for evaluating the mechanical behavior of the laboratory rocks from which the rock properties compressive strength and ductility are preferred for use in the characteristic function of the drill bit (Eq. (1)), it is within the scope and spirit of the present invention to employ other rock properties testing techniques and to incorporate into the characteristic function of the drill bit other measures of the rock mechanical behavior that are derived from the results of the rock properties tests.

What is claimed:

1. A method of determining rock compressive strength of a subterranean formation penetrated by a wellbore comprising:
   (a) obtaining a numerical model of a drill bit to be used to drill through the subterranean formation;
   (b) obtaining an estimate of the rock ductility of the subterranean formation;
   (c) measuring weight-on-bit (WOB) and bit rotational speed (RPM) as the drill bit drills through the subterranean formation; and
   (d) determining the rock compressive strength of the subterranean formation from the numerical model of the drill bit, the estimate of rock ductility, and weight-on-bit (WOB) and bit rotational speed (RPM).

2. The method of claim 1 wherein the numerical model includes empirically derived bit constants "a" related to bit tooth indentation, "b" related to bit tooth configuration, "c" related to fluid hydraulics across the bit, and "$\phi$" related to bit cone offset.

3. The method of claim 1 wherein rock ductility is determined from lithological information obtained from an adjacent wellbore that penetrates the subterranean formation.

4. The method of claim 1 wherein the rock compressive strength (step d) is determined on a real-time basis as the drill bit drills through the subterranean formation.

5. The method of claim 1 wherein rock compressive strength is determined using the following equation:

$$\sigma = \left[ \frac{W^2}{aD^2\epsilon} \left[ \frac{\frac{N}{R} - \frac{b}{D} - \frac{cN\rho\mu D}{I_m}}{d} + \frac{\phi^2}{4a\epsilon} \right] \right]^{.5} - \frac{\phi W}{2aD\epsilon^2}.$$

6. A method of generating a log of rock compressive strength comprising:

(a) obtaining numerical models of drill bits to be utilized in drilling a wellbore through subterranean formations;
(b) obtaining an estimate of rock ductility of the subterranean formations;
(c) measuring weight-on-bit (WOB) and bit rotational speed (RPM) as the drill bits pass through the subterranean formations;
(d) determining the rock compressive strength of the subterranean formations from the numerical models of the drill bits, the estimate of rock ductility, and weight-on-bit (WOB) and bit rotational speed (RPM); and
(e) outputting a depth correlated log of rock compressive strength.

7. The method of claim 6 wherein the depth correlated log of rock compressive strength is generated on a real-time basis while the wellbore is being drilled through the subterranean formations.

* * * * *

UNITED STATES PATENT AND TRADEMARK OFFICE
CERTIFICATE OF CORRECTION

PATENT NO. : 4,914,591

DATED : April 3, 1990

INVENTOR(S) : WARREN, ET AL

It is certified that error appears in the above--identified patent and that said Letters Patent is hereby corrected as shown below:

Column 4, line 10, "Units of Dimensions" should read --Units or Dimensions--.

Claim 5, column 6, in the equation, "$\frac{\phantom{x}}{d}$" should read -- $\frac{\phantom{x}}{D}$ --.

Signed and Sealed this

Tenth Day of March, 1992

*Attest:*

HARRY F. MANBECK, JR.

*Attesting Officer*      *Commissioner of Patents and Trademarks*